United States Patent [19]

Tajima et al.

[11] Patent Number: 4,739,090
[45] Date of Patent: Apr. 19, 1988

[54] PROCESS FOR PREPARING DIARYL-PENTAERYTHRITOL DIPHOSPHITES

[75] Inventors: Kenji Tajima, Kuwana; Masayuki Takahashi, Tokorozawa; Kazunori Nishikawa, Matsudo; Takashi Takeuchi, Urawa, all of Japan

[73] Assignee: Adeka Argus Chemical Co., Ltd., Urawa, Japan

[21] Appl. No.: 845,903

[22] Filed: Mar. 28, 1986

[30] Foreign Application Priority Data

Mar. 29, 1985 [JP] Japan ................................ 60-66300

[51] Int. Cl.⁴ .............................................. C07F 9/15
[52] U.S. Cl. .................................................. 558/78
[58] Field of Search .................... 558/78, 962, 101, 78

[56] References Cited

U.S. PATENT DOCUMENTS 3,772,414 11/1973 Baker et al. .......................... 558/101
4,312,818 1/1982 Maul et al. ............................ 558/96

FOREIGN PATENT DOCUMENTS 0159294 10/1985 European Pat. Off. ............. 558/78

*Primary Examiner*—Anton H. Sutto

[57] ABSTRACT

A process for preparing diaryl pentaerythritol diphosphites by reaction of phosphorous trichloride, pentaerythritol and an alkyl phenol having the formula

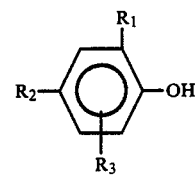

wherein:

$R_1$ is selected from the group consisting of tertiary alkyl having from about four to about eight carbon atoms and cyclohexyl; and $R_2$ and $R_3$ are each selected from the group consisting of hydrogen and alkyl having from one to about eight carbon atoms;

in the presence of a catalyst selected from the group consisting of amines; quaternary ammonium salts; amides of carboxylic acids; amides of oxygen acids of phosphorus; ureas; thioureas; and quaternary phosphonium salts.

27 Claims, No Drawings

PROCESS FOR PREPARING DIARYL-PENTAERYTHRITOL DIPHOSPHITES

Diaryl pentaerythritol diphosphites are known stabilizers for synthetic resins, and the ortho-alkylated phenyl derivatives are particularly useful due to their better hydrolytic stability.

Various processes for preparing diaryl pentaerythritol diphosphites have been suggested.

The reaction of aryl dichlorophosphite with pentaerythritol is disclosed in U.S. Pat. No. 2,847,443.

The reaction of phenols with dichloropentaerythritol diphosphite is disclosed in U.S. Pat. No. 3,192,243.

However, these processes are not suitable for preparing diaryl pentaerythritol diphosphites derived from phenols having a bulky substituent in the ortho position. It is difficult to obtain the pure hindered aryl dichlorophosphite starting material, and acid phosphites are easily produced in the reaction of hindered aryl dichlorophosphites with pentaerythritol. When the process of U.S. Pat. No. 3,192,243 is employed, the products contain high molecular weight impurities, because dichloropentaerythritol diphosphite is unstable itself, and furthermore, its reaction with hindered phenols is slow.

U.S. Pat. No. 4,312,818, patented Jan. 26, 1982, discloses a process for producing triarylphosphites of the formula $(RO)_3P$, in which R represents aryl or aryl substituted by one or more straight-chain or branched-chain alkyl, cycloalkyl, aryl or aralkyl groups, by reaction of phosphorous trihalides with hydroxy-substituted aromatic compounds of the formula ROH in the presence of 0.005 to 10 mol %, relative to the hydroxy-substituted aromatic compound, of a catalyst, optionally in the presence of a solvent, in which process the catalyst used is a compound from the group comprising amines or ammonium salts, amides of carboxylic acid and thiocarboxylic acids and also of oxygen acids of phosphorus, non-aromatic nitrogen-containing heterocycles and salts thereof, guanidines, amidines and azomethines and also salts thereof, sulfones, sulfoxides and sulfonium salts, primary, secondary and tertiary phosphines and salts thereof, phosphine oxides, phosphine sulfides or esters of phosphoric acids.

The reaction of tris(hindered phenyl)phosphites with pentaerythritol is disclosed in British Pat. No. 1,180,398. However, the process is not practical, because tris(hindered phenyl)phosphites cannot be easily prepared, and the reaction is very slow.

The reaction of diphenyl pentaerythritol diphosphite with dialkylphenols is disclosed in U.S. Pat. No. 4,305,866. However, in this process, phenol and dialkylphenols are also present in the reaction mixture, and therefore it is difficult to produce a pure product.

The reaction of hindered phenols, pentaerythritol and triphenylphosphite or phosphorous trichloride is disclosed in Japan Kokai No. 54-25951 ('79). However, no catalyst is disclosed.

In accordance with the process of this invention, hindered diaryl pentaerythritol diphosphites are prepared by reaction of phosphorous trichloride, pentaerythritol and an alkyl phenol having the formula

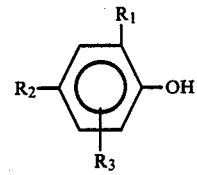

wherein:
$R_1$ is selected from the group consisting of tertiary alkyl having from about four to about eight carbon atoms and cyclohexyl; and
$R_2$ and $R_3$ are each selected from the group consisting of hydrogen and alkyl having from one to about eight carbon atoms;

in the presence of a catalyst selected from the group consisting of amines; quaternary ammonium salts; amides of carboxylic acids; amides of oxygen acids of phosphorus; ureas; thioureas; and quaternary phosphonium salts.

In the above formula, exemplary $R_1$ tertiary alkyl include t-butyl, t-amyl, t-hexyl, t-heptyl and t-octyl, and exemplary $R_2$ and $R_3$ alkyl include methyl, ethyl, propyl, isopropyl, butyl, isobutyl, sec-butyl, t-butyl, amyl, isoamyl, sec-amyl, t-amyl, hexyl, isohexyl, tert-hexyl, heptyl, isoheptyl, sec-heptyl, t-heptyl, octyl, isooctyl, 2-ethylhexyl, and t-octyl.

The catalyst used according to the invention is selected from the group consisting of amines; quaternary ammonium salts; amides of carboxylic acids; amides of oxygen acids of phosphorus; ureas; thioureas; and quaternary phosphonium salts. These catalysts are known, and are fully disclosed in U.S. Pat. No. 4,312,818, the disclosure of which is hereby incorporated by reference. See column 3, line 13 to column 5, line 52.

The amines include primary, secondary and tertiary amines, and acid salts thereof. Exemplary amines include methyl-, ethyl-, propyl-, n-butyl-, t-butyl-, pentyl-, octyl-, dodecyl-, phenyl-, benzyl-, dimethyl-, diethyl-, methylethyl-, methylbutyl-, methyloctyl-, trimethyl-, triethyl-, tributyl-, octyldimethyl- and dimethylphenyl-amine, pyrrolidine, pyrroline, N-methylpyrrolidine, dihydroindole, pyrazolidine, imidazolidine, pyrazoline, 1-phenylpyrazolidine, oxazolidine, thiazolidine, oxazoline, triazolidine, oxadiazolidine, thiadiazolidine, piperidine, morpholine, N-methylmorpholine, quinolidine, 1,2-dihydropurine, 8 aza-bicyclo(3,2,1)octane, 1,8-diaza-bicyclo(5,4,0)undecene-7, guanidine and tetramethylguanidine.

Examples of the quaternary ammonium salts are tetramethyl-, trimethylethyl, triethylmethyl, tributylmethyl-, tetrabutyl-, trimethyloctyl-, triphenylmethyl- and tribenzylmethyl-ammonium chloride, -bromide and -iodide.

Examples of amides of carboxylic acids are formamide, oxalic acid diamide, dimethylformamide, acetamide, thioacetamide, N,N-dimethylacetamide, N,N-dimethylthioacetamide, picolineanilide, thiopicolineanilide, benzoic acid amide, terephthalic acid diamide and trimellitic acid triamide.

Exemplary oxygen acids of phosphorus, from which the amides can be derived, are phosphoric acid, phosphorous acid, hypophosphorous acid, phosphonic acid, and phosphinic acid. Phosphoric acid and phosphonic acid are preferred. Examples of such amides are phosphoric acid triamide, hexamethylphosphoric acid triamide, methylphosphonic acid diamide, phenylphosphonic acid N,N-tetramethyldiamide, and N,N'-(dimethyl)-phenylphosphonic acid diamide.

Examples of ureas and thioureas which may be mentioned, in addition to urea and thiourea, are tetramethylurea and thiourea, diphenyl and dibenzylurea and thiourea, diethylurea, dioctylurea and thiourea, and also bisurea derivatives, for example, ethylene-bisurea and N,N-tetramethylphenylenethiourea. Examples of cyclic ureas are hydantoin and benzimidazolone.

Examples of quaternary phosphonium salts are tetramethyl-, trimethylethyl-, tributylmethyl-, triphenylmethyl- and tetraphenyl phosphonium chloride, -bromide and -iodide.

The molar ratio of the starting materials in the process of this invention are within the range from about 1.9 to about 2.5 moles, preferably from about 1.95 to about 2.2 moles, of phosphorous trichloride, and more than 2 moles, preferably within the range from about 2.0 to about 2.5 moles, of alkylphenol, per mole of pentaerythritol. The amount of catalyst to be used is within the range from about 0.005 to about 10, preferably from about 0.01 to about 3, weight % of pentaerythritol employed.

The desired compounds can be prepared in accordance with this invention in high yield and in high purity. It is preferred to use an organic oxygen acid of phosphorus as a co-catalyst, to obtain the product with greater purity.

The organic oxygen acid of phosphorus co-catalysts include mono and diesters of phosphoric acid, organic phosphonic acids, and monoesters of organic phosphonic acids and organic phosphinic acids.

Examples of mono and diesters of phosphoric acid are diphenylphosphate, monophenylphosphate, dicresylphosphate, di(dimethylphenyl)phosphate, monomethylphosphate, dimethylphosphate, di-n-butyl-phosphate, di(p-t-octylphenyl)phosphate, di(2-ethylhexylphenyl)phosphate, di-2-ethylhexylphosphate, mono-2-ethylhexylphosphate, di-iso-octylphosphate, mono-isooctylphosphate, mono-decylphosphate, monododecylphosphate, 2-ethylhexyl-phenylphosphate, 2-ethylhexyl-p-t-octylphenylphosphate, dicyclohexylphosphate, monocyclohexylphosphate, di(tetrahydrofurfuryl)phosphate, difurylphosphate, di(2-cyclohexylphenyl)phosphate, di-α-naphthyl phosphate, di(biphenyl)phosphate, dibenzylphosphate and monobenzylphosphate.

Examples of organic phosphonic acids and monoesters of organic phosphonic acids are phenyl phosphonic acid, 2-ethylhexyl phosphonic acid, n-butyl phosphonic acid, isoamyl phosphonic acid, cyclohexyl phosphonic acid, α-naphthyl phosphonic acid, benzyl phosphonic acid, 2-phenylethyl phosphonic acid, tolyl phosphonic acid, 2-cyclohexyl phosphonic acid, biphenyl phosphonic acid, phenylethyl phosphonate, 2-ethylhexyl phenyl phosphonate, di(2-ethylhexyl)phosphonate, di(-tolyl)phosphonate, diphenyl phosphonate, di(cyclohexyl)phosphonate and di(tetrahydrofurfuryl)phosphonate.

Examples of organic phosphinic acids are diphenylphosphinic acid, di-2-ethylhexylphosphinic acid, di(t-octylphenyl)phosphinic acid, 2-ethylhexyl-phenylphosphinic acid, isodecyl-2-ethylhexylphosphinic acid, di-n-propylphosphinic acid, di-α-naphthyl phosphinic acid, di(cyclohexyl)phosphinic acid, di(tolyl)phosphinic acid, dibenzylphosphinic acid, biphenyl-phenylphosphinic acid, di(biphenyl)phosphinic acid, 2-ethylhexyl-t-octylphenylphosphinic acid and di(dimethylphenyl)-phosphinic acid.

The amount of co-catalyst is within the range from about 0.005 to about 10, preferably from about 0.01 to about 3, weight % of pentaerythritol.

The process according to the invention can be carried out without a solvent. The concomitant use of a solvent, however, has proved to be advantageous in many cases. Suitable solvents are, for example, aromatic and aliphatic hydrocarbons, such as benzene, toluene, xylene, ethylbenzene, cumene, pseudocumene, cymene, hexane, heptane, octane and mineral spirits; aliphatic and cyclic ethers, such as diethylether, tetrahydrofurane, dioxane, monoglyme and diglyme; and halogenated aliphatic and aromatic hydrocarbons such as perchloroethylene, chlorobenzene and dichlorobenzene.

The process according to the invention can be carried out at a temperature within the range from about 20° to about 200° C., preferably from about 50° to about 150° C.

The diarylpentaerythritol diphosphites (DAPP) prepared by the process of this invention have either a spiro structure, e.g.

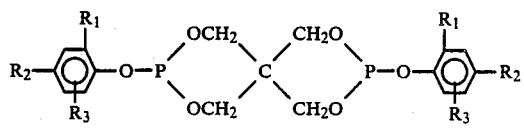

or a cage structure, e.g.

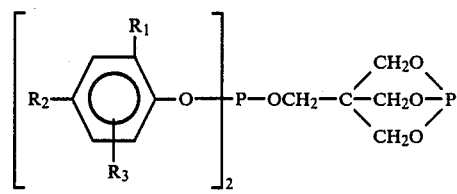

In the usual case, the DAPP prepared by the process of this invention is a mixture of a major amount of the spiro compound and a minor amount (normally less than 10 weight %) of the cage compound.

The impurities which may be present in the DAPP include triaryl phosphites (TAP), unreacted alkylphenols (AP), and others. The amount of these impurites is determined by liquid chromatograph and gas chromatograph, in the Examples.

The following Examples represent preferred embodiments of the invention.

EXAMPLES 1 TO 6

2,4-Di-t-butylphenol 226.9 g (1.1 moles), pentaerythritol 68.1 g (0.5 mole), 0.68 g of the catalyst as shown in Table I and 300 g of xylene were stirred at 90° C., and 137.4 g of phosphorous trichloride was added dropwise over two hours.

The mixture was then stirred for additional 10 hours (20 hours when no catalyst used) at 90° C. The solution was then filtered, and the solvent and excess alkylphenol were distilled off under vacuum. The product was obtained as a white solid.

The amount of the product, composition and yield of DAAP are reported in Table I.

TABLE I

| Example No. | Catalyst | Amount of Product (g) | Composition (%) | | | | Yield of DAAP (%) |
|---|---|---|---|---|---|---|---|
| | | | DAAP | TAP | AP | Others | |
| Control 1 | None | 214.7 | 72.5 | 4.8 | 0.8 | 21.9 | 51.5 |
| Example 1 | Triethylamine | 287.2 | 88.9 | 3.6 | 0.3 | 7.2 | 84.5 |
| Example 2 | Tributylamine | 288.6 | 87.5 | 3.7 | 0.3 | 8.5 | 83.6 |
| Example 3 | Tetrabutylammonium bromide | 282.0 | 86.2 | 3.8 | 0.4 | 9.6 | 80.5 |
| Example 4 | Dimethylformamide | 283.8 | 86.6 | 3.7 | 0.3 | 9.4 | 81.4 |
| Example 5 | Tetramethylthiourea | 275.4 | 85.8 | 4.1 | 0.5 | 9.6 | 78.2 |
| Example 6 | Tetramethylphosphonium bromide | 281.5 | 86.0 | 3.6 | 0.4 | 10.0 | 80.2 |

It is apparent from the above data that a catalyst is essential for optimum yield.

EXAMPLES 7 TO 12

2,4-Di-t-butylphenol 226.9 g (1.1 moles), pentaerythritol 68.1 g (0.5 mole), 0.34 g of triethylamine and 0.17 g of organic oxygen acid of phosphorus as shown in Table II as catalyst, and 300 g of xylene were stirred at 90° C., and 137.4 g of phosphorous trichloride was added dropwise over two hours.

The mixture was then stirred for additional 10 hours (20 hours when no catalyst used) at 90° C. The solution was then filtered, and the solvent and excess alkylphenol were distilled off under vacuum. The product was obtained as a white solid.

The amount of the product, composition and yield of DAAP are reported in Table II.

TABLE II

| Example No. | Organic oxygen acid of phosphorus | Amount of Product (g) | Composition (%) | | | | Yield of DAAP (%) |
|---|---|---|---|---|---|---|---|
| | | | DAAP | TAP | AP | Others | |
| Control 1 | Mono/di-methylphosphate (0.51 g, without triethylamine) | 225.8 | 75.2 | 4.5 | 0.6 | 19.7 | 56.2 |
| Control 2 | None (0.51 g of triethylamine was used) | 279.5 | 86.0 | 4.8 | 0.3 | 8.9 | 79.6 |
| Example 7 | Mono/di-methylphosphate (1:1) | 295.4 | 94.3 | 2.3 | 0.1 | 3.3 | 92.2 |
| Example 8 | Monodecylphosphate | 291.3 | 94.5 | 2.2 | 0.1 | 3.2 | 91.2 |
| Example 9 | Phenylphosphonic acid | 292.6 | 92.7 | 3.3 | 0.1 | 3.9 | 89.8 |
| Example 10 | Monobenzylphosphonate | 292.0 | 91.4 | 4.0 | 0.2 | 4.4 | 88.4 |
| Example 11 | Diphenylphosphate | 293.7 | 93.8 | 2.8 | 0.1 | 3.3 | 91.2 |
| Example 12 | Di(2-ethylhexyl)-phosphinic acid | 290.5 | 91.6 | 3.9 | 0.2 | 4.3 | 88.1 |

It is apparent from the above data that a catalyst is essential for optimum yield.

EXAMPLES 13 TO 18

Pentaerythritol 68.1 g (0.5 mole), 1.1 mole of alkylphenol as shown in Table III, xylene 300 g, triethylamine 0.34 g and mono/di-methylphosphate (1:1) 0.17 g were stirred at 90° C. Then, 137.4 g (1.0 mole) of phosphorous trichloride was added dropwise over two hours, followed by stirring an additional 10 hours at 90° C.

The solution was then filtered, and the solvent and excess alkylphenol were distilled off under vacuum. The product was obtained as a white solid.

The amount of the product, composition and yield of DAAP are reported in Table III.

TABLE III

| Example No. | Alkylphenol | Amount of Product (g) | Composition (%) | | | | Yield of DAAP (%) |
|---|---|---|---|---|---|---|---|
| | | | DAAP | TAP | AP | Others | |
| Example 13 | 2-t-Butyl-5-methylphenol | 247.4 | 90.5 | 5.1 | 0.3 | 4.2 | 86.1 |
| Example 14 | 2-t-Butyl-4-methylphenol | 248.5 | 91.3 | 4.8 | 0.3 | 3.6 | 87.3 |
| Example 15 | 2-t-Amyl-4-methylphenol | 244.7 | 88.6 | 5.0 | 0.4 | 6.0 | 81.2 |
| Example 16 | 2-Cyclohexylphenol | 250.6 | 89.5 | 4.4 | 0.4 | 5.7 | 82.5 |
| Example 17 | 2-t-Butyl-4,6-dimethylphenol | 240.9 | 88.2 | 4.1 | 0.4 | 7.3 | 79.6 |
| Example 18 | 2,4-Di-t-octylphenol | 366.4 | 83.6 | 3.7 | 1.8 | 10.9 | 74.0 |

COMPARATIVE EXAMPLE

Triphenyl phosphite 310.3 g (1.0 mole), pentaerythritol 68.1 g (0.5 mole) and 3.0 g sodium methoxide were stirred at 130° to 160° C., and the theoretical amount of phenol distilled off under vacuum, resulting in diphenylpentaerythritol diphosphite. 2,4-Di-t-butylphenol 226.9 g (1.1 moles) was added and stirred at 190° C./5 mm Hg (max.) while distilling off the liberated phenol. 93 g phenol (99% of theoretical) was distilled off over 10 hours, and then excess 2,4-di-t-butylphenol was removed at 210° C./5 mm Hg.

The product obtained, 296.4 g of white solid, contained 74.3% of DAPP, 2.4% of TAP, 0.5% of AP and 18.8% of others. The yield of DAPP was 72.9%.

Having regard to the foregoing disclosure the following is claimed as the inventive patentable embodiments thereof:

1. A process for preparing hindered diaryl pentaerythritol diphosphites, which comprises reacting at a temperature within the range from about 20° to about 200° C. phosphorous trichloride in an amount within the range from about 0.1 to about 2.5 moles, pentaerythritol, and, in an amount of at least 2 moles per mole of pentaerythritol, an alkyl phenol having the formula:

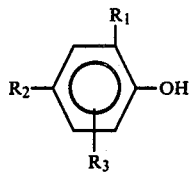

wherein:
   $R_1$ is selected from the group consisting of tertiary alkyl having from about four to about eight carbon atoms and cyclohexyl; and
   $R_2$ and $R_3$ are each selected from the group consisting of hydrogen and alkyl having from one to about eight carbon atoms; in the presence of a catalyst selected from the group consisting of amines; quaternary ammonium salts; amides of carboxylic acids; amides of oxygen acids of phosphorus; ureas; thioureas; and quaternary phosphonium salts, the catalyst being in an amount within the range from about 0.05 to about 10% by weight of the amount of pentaerythritol.

2. A process according to claim 1 in which $R_1$ is t-butyl.

3. A process according to claim 1 in which $R_1$ and $R_2$ are each t-butyl.

4. A process according to claim 1 in which $R_1$ is t-amyl.

5. A process according to claim 1 in which $R_1$ is t-octyl.

6. A process according to claim 1 in which $R_1$ and $R_2$ are each t-octyl.

7. A process according to claim 1 in which $R_1$ is cyclohexyl.

8. A process according to claim 1 in which $R_2$ is methyl.

9. A process according to claim 1 in which $R_1$ is t-butyl and $R_2$ is methyl.

10. A process according to claim 1 in which $R_1$ is t-amyl and $R_2$ is methyl.

11. A process according to claim 1 in which $R_3$ is methyl.

12. A process according to claim 1 in which $R_1$ is t-butyl and $R_3$ is methyl.

13. A process according to claim 1 in which $R_1$ is t-butyl and $R_2$ and $R_3$ are each methyl.

14. A process according to claim 1 in which the reaction temperature is within the range from about 50° to about 150° C.

15. A process according to claim 1 carried out in the presence of a solvent.

16. A process according to claim 15 in which the solvent is an aliphatic or aromatic hydrocarbon.

17. A process according to claim 15 in which the solvent is an aliphatic or cyclic ether.

18. A process according to claim 15 in which the solvent is a halogenated aliphatic or aromatic hydrocarbon.

19. A process according to claim 1 carried out in the presence of a co-catalyst.

20. A process according to claim 19 in which the co-catalyst is an organic oxyacid of phosphorus.

21. A process according to claim 1 in which the catalyst is an amine.

22. A process according to claim 1 in which the catalyst is a quaternary ammonium salt.

23. A process according to claim 1 in which the catalyst is a carboxylic acid amide.

24. A process according to claim 1 in which the catalyst is an amide of an oxyacid of phosphorus.

25. A process according to claim 1 in which the catalyst is urea.

26. A process according to claim 1 in which the catalyst is thiourea.

27. A process according to claim 1 in which the catalyst is a quaternary phosphonium salt.

* * * * *